(12) United States Patent
Forstner

(10) Patent No.: US 6,929,610 B2
(45) Date of Patent: Aug. 16, 2005

(54) NON-INVASIVE MEASUREMENT OF BLOOD PRESSURE

(75) Inventor: Klaus Forstner, Tamm (DE)

(73) Assignee: Microlife Intellectual Property GmbH, Heerbrugg (CH)

(*) Notice: Subject to any disclaimer, the term of this patent is extended or adjusted under 35 U.S.C. 154(b) by 50 days.

(21) Appl. No.: 10/475,519

(22) PCT Filed: Mar. 25, 2002

(86) PCT No.: PCT/EP02/03300

§ 371 (c)(1),
(2), (4) Date: Oct. 28, 2003

(87) PCT Pub. No.: WO02/091919

PCT Pub. Date: Nov. 21, 2002

(65) Prior Publication Data

US 2004/0097815 A1 May 20, 2004

(30) Foreign Application Priority Data

May 14, 2001 (EP) .............................. 01810474

(51) Int. Cl.$^7$ ................................. A61B 5/02
(52) U.S. Cl. ....................... 600/485; 600/500
(58) Field of Search ............................ 600/481, 485, 600/486, 490–496, 500–503

(56) References Cited

U.S. PATENT DOCUMENTS

| | | | |
|---|---|---|---|
| 4,517,986 A | 5/1985 | Bilgutay | |
| 4,667,680 A | 5/1987 | Ellis | |
| 4,747,412 A | 5/1988 | Yamaguchi | |
| 4,850,368 A | 7/1989 | Miyawaki | |
| 4,984,577 A | * 1/1991 | Frankenreiter | 600/494 |
| 5,014,714 A | 5/1991 | Millay et al. | |
| 5,404,878 A | * 4/1995 | Frankenreiter et al. | 600/493 |
| 5,590,661 A | 1/1997 | Ohmori et al. | |
| 5,649,536 A | 7/1997 | Ogura et al. | |
| 5,752,919 A | 5/1998 | Schrimpf | |
| 6,045,510 A | 4/2000 | Ogura et al. | |
| 6,233,486 B1 | * 5/2001 | Ekwall et al. | 607/17 |
| 6,475,153 B1 | * 11/2002 | Khair et al. | 600/485 |

FOREIGN PATENT DOCUMENTS

| | | |
|---|---|---|
| EP | 0342249 | 11/1989 |
| EP | 0342249 | 1/1991 |
| EP | 0536782 | 4/1993 |

* cited by examiner

*Primary Examiner*—Robert L. Nasser
*Assistant Examiner*—Navin Natnithithadha
(74) *Attorney, Agent, or Firm*—Shoemaker and Mattare

(57) ABSTRACT

By a method to measure the blood pressure of a patient, a series of measurements for the diastolic, the systolic blood pressure and for the pulse rate are made. The results are analysed in order to determine, and to display whether the patient is properly settled to a rest condition, and whether the patients blood pressure variation is found as being normal. Further it is investigated, whether there are high measurement result alterations due to artefacts. Highly altered results are excluded. If the results are sufficiently similar, an average of the result is made. If the results are not sufficiently similar, but still below pre-defined alteration limits, a weighted average is applied to the systolic and the diastolic blood pressure.

11 Claims, 4 Drawing Sheets

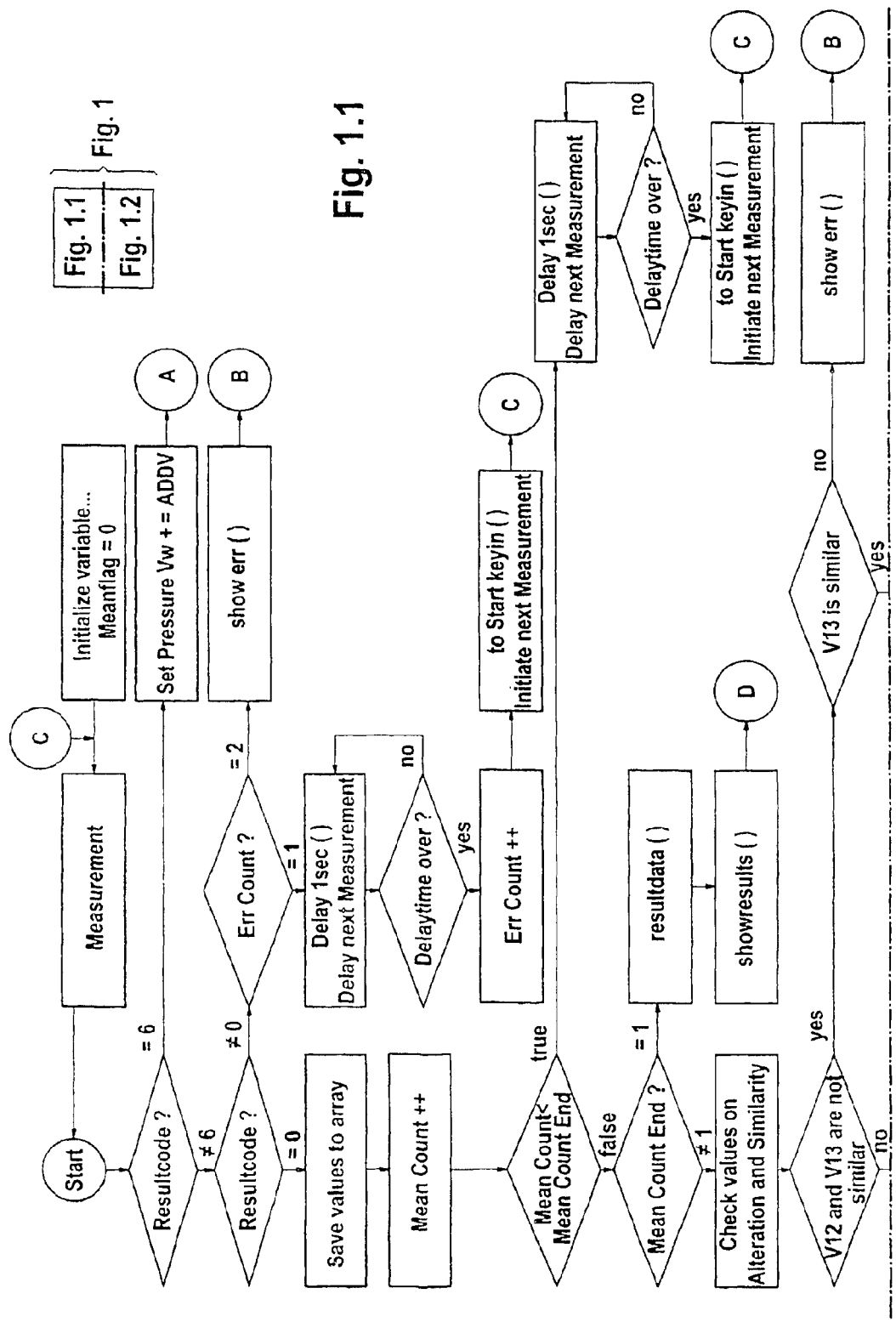

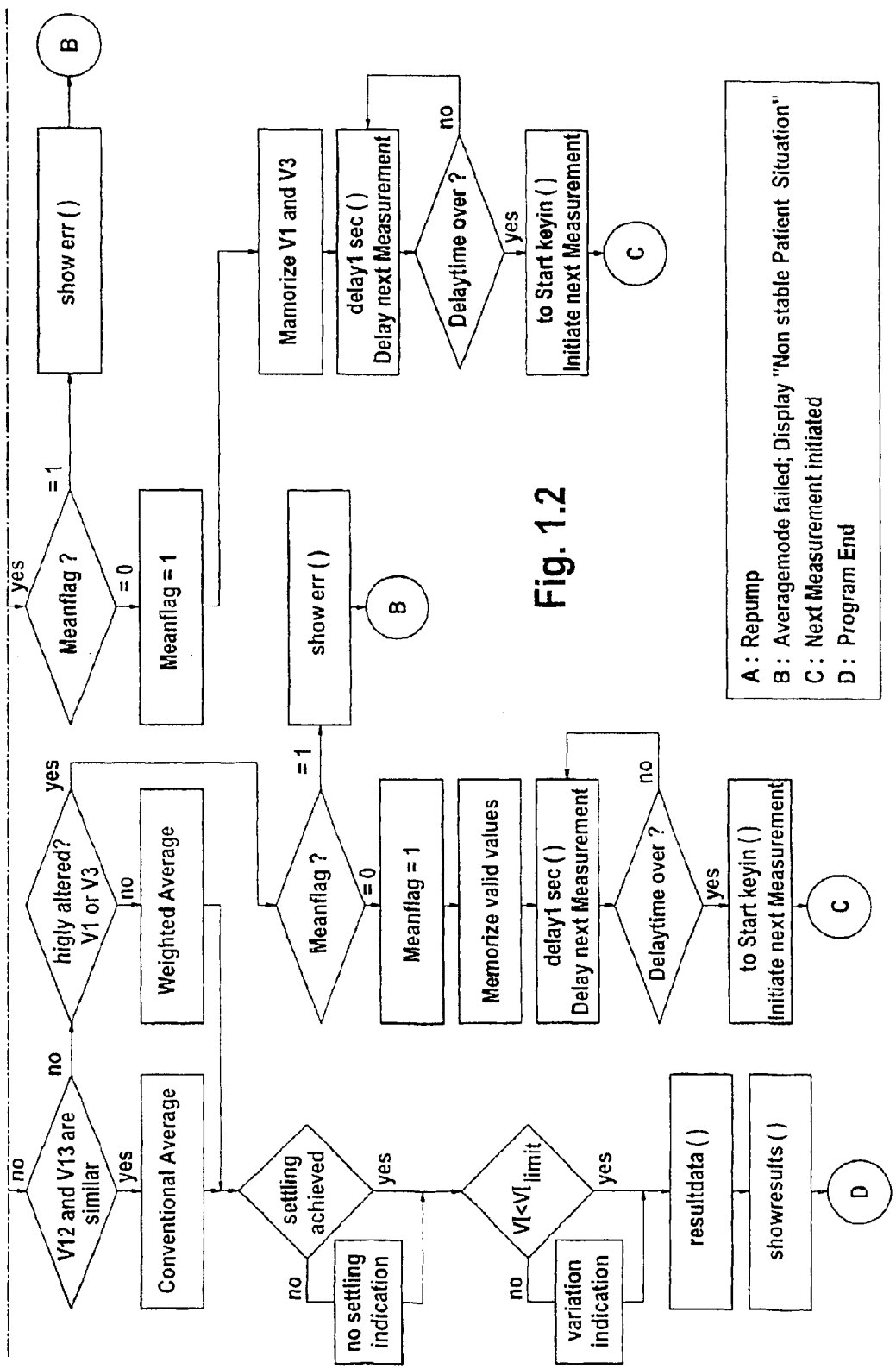
Fig. 1.2

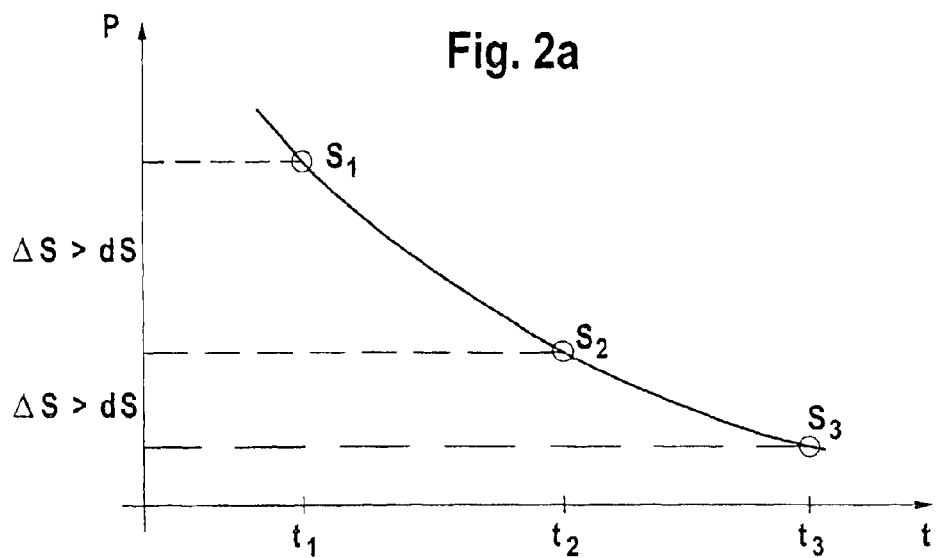
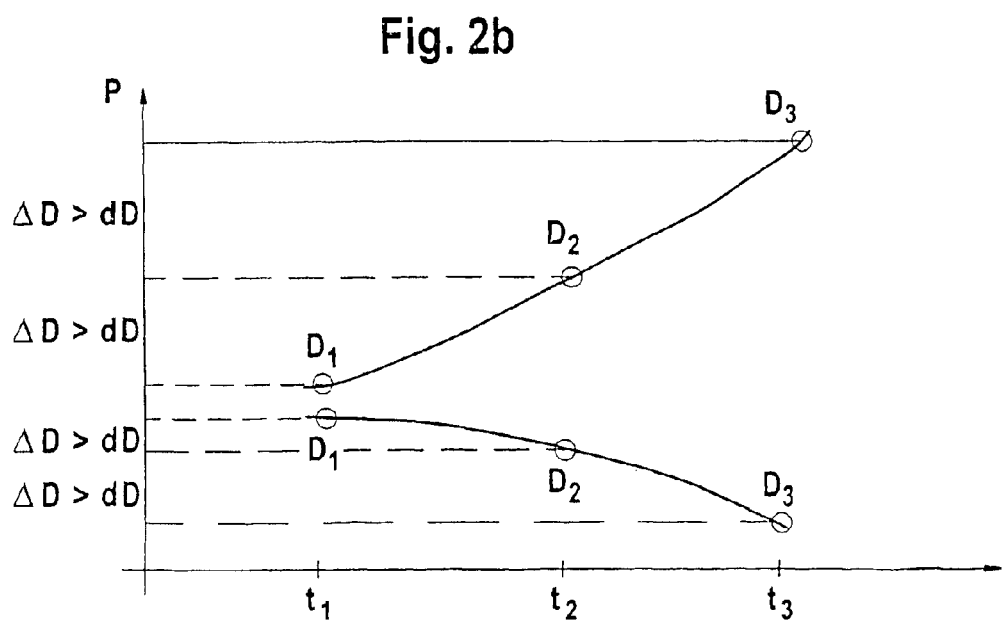

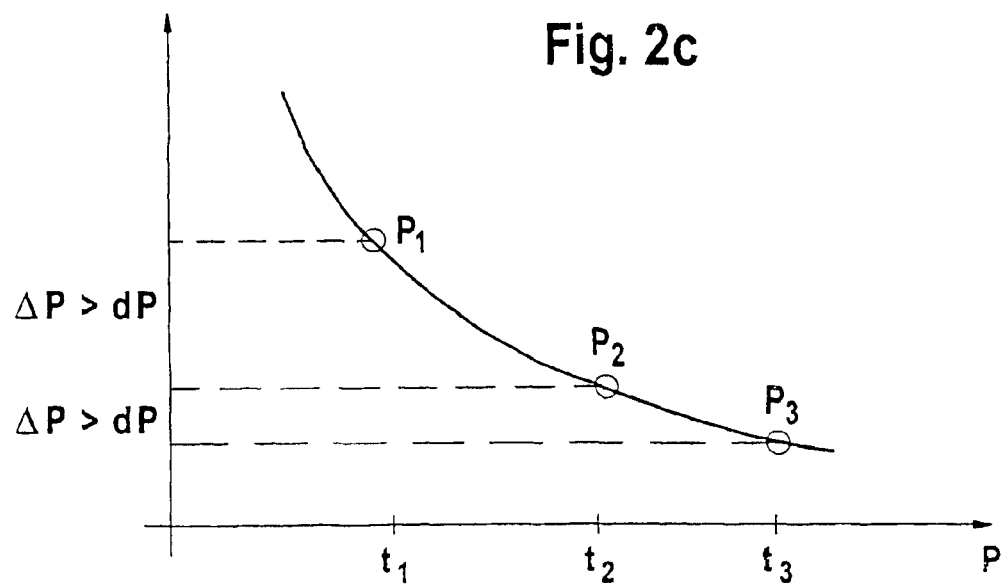
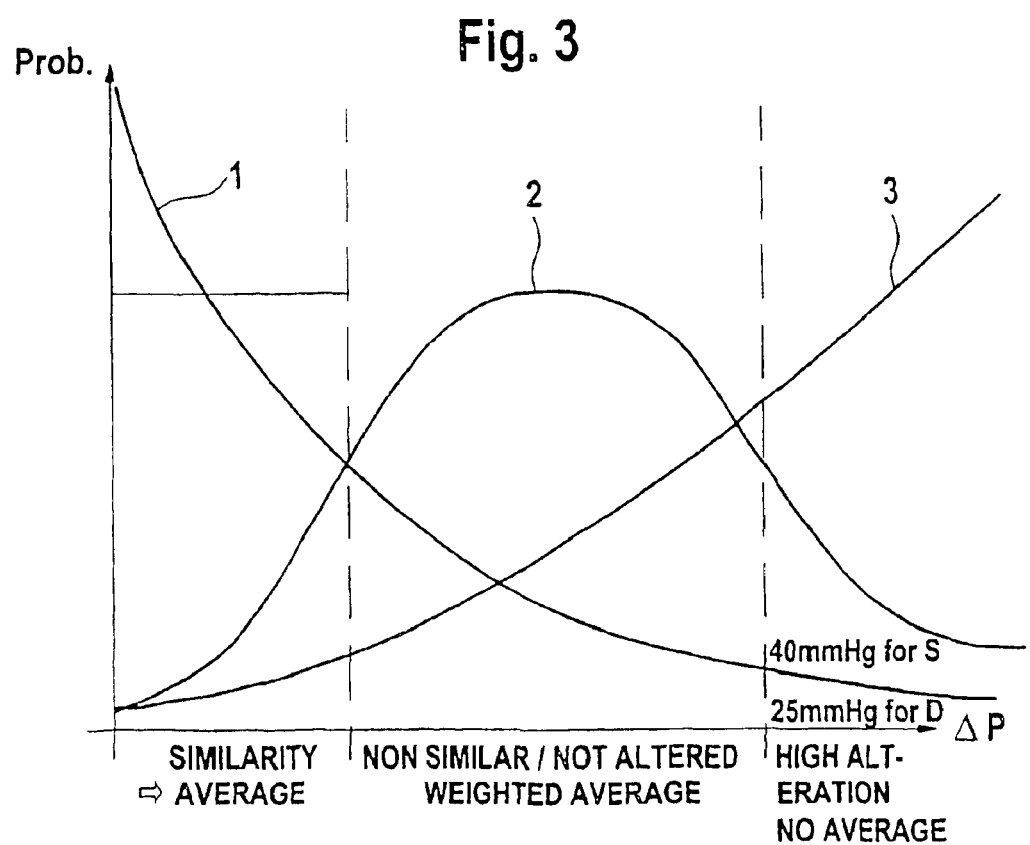

NON-INVASIVE MEASUREMENT OF BLOOD PRESSURE

BACKGROUND OF THE INVENTION

1. Field of the Invention

The invention relates to a method and a device for non-invasively measuring the blood pressure of a patient.

2. Description of Related Art

Automatic electronic blood pressure monitors for non-invasively measuring the blood pressures are widely known. Such monitors determine the value of the systolic and the diastolic blood pressure e.g. on the basis of an oscillometric measurement. During such a measurement, the pressure within an inflated cuff wrapped around the arm of a patient is measured during deflation of the cuff. The systolic and the diastolic blood pressure and optionally the pulse rate are determined on the basis of the variation of the cuff pressure.

Automatic, electronic blood pressure measuring devices are usually applied to the upper arm of a patient, around the wrist or to a finger of the patient. There are always specific causes for errors during such measurements. Inaccurate measurement results may be due to normal physiological changes, insufficient rest condition of the patient, to pathologic blood pressure changes or to technical or application related artifact. For example application artifact may be caused by movements of the application site during the measurement cycle. The errors created by insufficient rest condition and by motion artifact could be avoided if the patient correctly follows the user instructions of such a measuring device. It is, however, often the case, that measurements are carried out with the patient being not at a sufficient rest condition or patient application sites are moving during the measurement. This may lead to incorrect measurement results.

This problem has already been addressed in the copending European patent application EP-99122743.9 of the same inventors.

BRIEF SUMMARY OF THE INVENTION

It is an object of the present invention to overcome the draw-backs of the prior art, especially to provide an automatic, non-invasive blood pressure monitor and a method for measuring the blood pressure, which allow to reduce such incorrect measurement results. It is a further object of the invention to detect pathologic blood pressure changes during a blood pressure measurement.

According to the present invention, these objects are solved with a method and a device for non-invasively measuring the blood pressure of a patient as described below.

There are mainly four reasons for sequential blood pressure values differing from each other. Differences may be due to normal physiologic changes, due to an insufficient rest condition of the patient or to pathologic blood pressure changes. Pathologic changes may derive from a broad variety of cardiovascular disorders. Finally, changes may be due to artifact. Technical artifact, i.e. disturbances caused by the device and application artifact, e.g. artifact caused by the motion of the patient are observed.

For each difference between sequential measurement results, there is a specific probability for every cause.

Low differences without a specific tendency occur mainly due to physiologic changes of the arterial blood pressure. Low to moderate differences, which follow specific dynamic changes known to those skilled in the art may be an indication of an insufficient patient rest condition. Normally, in such a case, the measurement results of the diastolic pressure rise while the values of the systolic pressure and the pulse frequency fall during a sequence.

Moderate changes occur due to a broad variety of pathologic blood pressure disorders. High changes are mostly due to artifact.

The present invention allows to enhance the judgement of blood pressure measurement results. Especially, the invention allows to distinguish errors caused by artifact from errors caused by pathologic and/or physiologic variations. In addition, the present invention allows to determine, whether or not a patient is properly settled to rest condition.

According to the method of the present invention, in a first step, the diastolic and the systolic blood pressure value and the pulse rate of a patient are non-invasively measured, preferably with the oscillometric method. The oscillometric method is known to those skilled in the art and does not need to be explained in detail.

After measuring the diastolic, the systolic blood pressure value and the pulse rate in a first step a.); step a.) is repeated at least once. Thereby, a series of consecutive results of the values of the systolic and the diastolic blood pressure and of the pulse rate are produced. Calculations, e.g. averages, of the values as defined below are performed subsequently.

In a further step, these series of consecutive results are automatically analysed for determining the validity of the results. During this analysis, it is verified, whether the results fulfil one or more of the following conditions:

Condition i.): it is verified, whether the results of the diastolic or the systolic blood pressure and of the pulse rate are steadily decreasing or increasing. If the value for the systolic blood pressure is continously decreasing over the consecutive measurements or if the value for the diastolic blood pressure is continously increasing or decreasing during the measurements and if at the same time the pulse rate is continously decreasing during the measurement, it is concluded that the patient is not at a sufficient rest condition. Continuously decreasing/increasing is defined as follows, referring to a three measurement analysis:

$$Si - S(i-1) < Si, i-1 \qquad (A)$$

$$Di - D(i-1) < Di, i-1 \qquad (B1)$$

$$Di - D(i-1) > Di, i-1 \qquad (B2)$$

$$Pi - P(i-1) < Pi, i-1 \qquad (C)$$

with typical constants:

$$S32 = S21 = -5 [mmHg]$$

$$D32 = D21 = -3 [mmHg] \text{ or } +3 (mmHg)$$

$$P32 = -3 [bpm]$$

$$P21 = -5 [bpm]$$

Condition i.) is met if either (A) AND (B1) AND (C) or (A) AND (B2) AND (C) holds valid.

Condition ii.): according to a preferred embodiment of the invention, a variation index of the series of the results of the values of the diastolic blood pressure, the systolic blood pressure and the pulse rate according to the following formula is formed respectively:

$$VI = \frac{1}{n}\sum_{i=1}^{n}\frac{|R_i - \text{mean}|}{\text{mean}} = \frac{1}{n}\sum_{i=1}^{n}\frac{\left|R_i - \sum\frac{Ri}{n}\right|}{\sum\frac{Ri}{n}} = \frac{1}{n}\sum_{i=1}^{n}\frac{\left|R_i - \sum R_i\right|}{\sum R_i}$$

$$\text{whereby mean} = \sum_{i=1}^{n}\frac{R_i}{n}$$

and whereby Ri are the results of the respective measurements of the diastolic, systolic blood pressure and of the pulse rate and whereby n is the number of subsequent measurements. The variation index is determined for all values of the systolic, the diastolic blood pressure and the pulse rate. The variation index is a figure which describes the measurement stability. If the variation index is high, this may be due to a cardiovascular disorder, affecting the blood pressure stability, e.g. deriving from arrythmia, heart insufficiency or a vascular control disorder. The variation index for each of the results is therefore compared with a predetermined or predeterminable variation index limit. If the variation index is above this limit, the patient/user is informed by displaying this particular result. The patient/user is advised to have a new measurement run.

Condition iii.): according to a further preferred embodiment of the invention, it is verified, whether the differences between the consecutive measurement results of the systolic blood pressure and of the diastolic blood pressure are below a predetermined or predeterminable similarity limit. The similarity limit may be e.g. set to +/−12 mmHg for the diastolic blood pressure and +/−18 mmHg for the systolic blood pressure. If the differences are below the similarity limit, it is assumed that the blood pressure results are sufficiently similar to each other. In this case, a normal arithmetic average is formed on the basis of the results of the measurements of the systolic and of the diastolic blood pressure.

Condition iv.): according to a further preferred embodiment, it is verified where the differences between the consecutive measurement results of the systolic and diastolic blood pressure are above a predetermined alteration limit. The alteration limit may be typically set to +/−25 mmHg for the diastolic blood pressure and to +/−40 mmHg for the systolic blood pressure. If one of the blood pressure measurement results is beyond this limit, it is assumed that this result is highly altered and is due to artifact. Such results therefore are disregarded in the measuring sequence.

Results which are above the similarity limits as defined in condition iii but which are not above the alteration limit as defined in condition iv may be caused by pathologic cardiovascular events but may also be induced by artifact. These results are probably not fully correct and therefore are not completely disregarded. The influence of these values is reduced by applying a weighted average of the results of the measurement. Thus, the suspicious results are not contributing as high as the normal results. By this measure, possible artifact are reduced.

Results not exceeding the similarity limit as defined in condition iii are likely to be correctly measured results. They are used to calculate a classic average result.

Typically, a series of three measurements is made. If one of the results is disregarded, a fourth measurement may be made for generating three usable results. If an artifact is specifically detected by the measurement device, one repetition occurs. So the maximum of blood pressure takes is 5, comprising 3 measurements, one possible artifact-induced repetition and one possible variation-induced repetition. Larger number of measurements could also be made. Three measurements are, however, preferred in order to limit the complete measurement period, which should not exceed 5 to 7 minutes in practice.

The device according to the present invention is non-invasively measuring the blood pressure of a patient in the above described manner. For that purpose, the device is provided with means for determining the diastolic and the systolic blood pressure and the pulse rate of the patient with the oscillometric method.

The device is further provided with means for storing a series of consecutive measurement results of the systolic and the diastolic blood pressure and of the pulse rate. The device includes means for analyzing the series of consecutive results of the diastolic and systolic blood pressure and of the pulse rate. The means for analyzing the results are adapted to determine whether the results of the diastolic or the systolic blood pressure are steadily decreasing or increasing and whether at the same time the results of the pulse rate are decreasing.

According to a preferred embodiment, the means for analyzing are further adapted to determine a variation index as defined above and for comparing the variation index with a predetermined or preterminable variation index limit.

According to another preferred embodiment, the means for analyzing are adapted to determine whether the results of a series of measurements for the systolic and diastolic blood pressure, pulse rate or below/above predetermined or predeterminable similarity limits and/or alteration limits, respectively.

The device according to the present invention is further provided with means for calculating an average or a weighted average on the basis of a series of consecutive measurement results The invention will be more clearly understood with reference to the following embodiments and to the following drawings, which show:

BRIEF DESCRIPTION OF THE DRAWINGS

FIG. 1: a flow chart of the method according to the present invention.

FIGS. 2a to 2c: a graphic representation of the rest condition detection.

FIG. 3: a graphic representation of similarity/alteration detection.

DETAILED DESCRIPTION OF THE INVENTION

According to the present invention, for the measurement of the blood pressure, a number of consecutive measurements is made. Typically, three measurements, and under certain conditions, up to five measurements, are made to obtain the diastolic blood pressure D, the systolic blood pressure S and the pulse rate P. Each measurement lasts for about 60 seconds. Between two subsequent measurements, a pause of another 45–60 seconds is made. This is necessary because between two measurements, the venous reflow has to be completed. According to actual findings in medicine, this requires a minimum period of about 45 seconds.

The three measurements generate a series of measurement results D1, D2, D3 representing the diastolic blood pressure value, S1, S2, S3 representing the systolic blood pressure value and P1, P2, P3 representing the pulse rate. These values are stored within the blood pressure measuring device.

After three successful measurements an average is calculated (see below) and an analysis of the measurement results is made.

In a first step, it is verified, whether or not the patient is in a proper rest condition. For that purpose, it is verified whether a first condition i.) as follows is fulfilled:
Systolic Criteria for Condition i.):

$$S3 < S2 - dS < S1 - 2dS \qquad (A)$$

whereby dS is approximately set to 5 mmHg
Diastolic Criteria for Condition i.)

$$D3 > D2 + dD > D1 + 2dD \text{ or} \qquad (B1)$$

$$D3 < D2 - dD < D1 - 2dD \qquad (B2)$$

whereby dD is set to about 3 [mmHg]
Pulse Rate Criteria for Condition i.)

$$P3 < P2 - dP2 \text{ AND } P2 < P1 - dP1 \qquad (C)$$

whereby dP1 is set to about 5 [Bpm] (beats per minute), and dP2 is about 3 [Bpm]. The change of the pulse rate is decreasing in the course of time when a patient is not at a rest condition. For this reason, dP1 is set higher than dP2.

A patient is detected as being not properly settled, if the systolic criteria (A) AND one of the diastolic criteria (B1) OR (B2) AND the pulse rate criteria (C) are fulfilled.

The behaviour of the systolic blood pressure, the diastolic blood pressure and the pulse rate in case of an insufficient rest condition are schematically shown in FIGS. 2a to 2c.

According to FIG. 2a, the systolic blood pressure is continously decreasing from the first to the third measurement result. The difference S between subsequent blood pressure values S1 and S2 and S2, S3 are above the preset limit of the parameter dS.

FIG. 2b shows the behaviour of the diastolic blood pressure if a patient is not properly settled to rest condition. In such cases, the diastolic pressure is usually increasing steadily towards a steady state value in the course of the three measurements. According to FIG. 2b, the values D1, D2 and D3 are steadily increasing. The difference D between D2, D1 and between D3, D2 are both above the predetermined limit of change dD.

In some cases, the diastolic blood pressure values of a person, who is not properly settled, are decreasing towards a steady state value D3*. In this case D1* is larger than D2* which is larger than D3*.

Both conditions are observed in persons, being not properly settled.

FIG. 2c shows the dynamics of the pulse rate of a patient who is still not properly settled.

The values of the pulse rate are steadily decreasing towards a steady state value. The difference P between the subsequent measurements P1, P2 and P2, P3 is above a predetermined limit dp.

If the conditions shown in FIG. 2a or 2b are fulfilled AND the condition in FIG. 2c holds valid as well, it is concluded that the patient is not properly settled.

The patient/user is informed about that fact and advised to have another measurement procedure after being intentionally in rest condition.

In a further step, it is verified by condition ii.), whether or not the measurement results disclose an indication of a disorder of the blood pressure stability. For that purpose, a variation index according to the following formula is applied to the diastolic, the systolic blood pressure and to the pulse rate:

$$VI = \frac{1}{n}\sum_{i=1}^{n}\frac{|R_i - \text{mean}|}{\text{mean}}$$

$$\text{whereby mean} = \sum_{i=1}^{n}\frac{R_i}{n}$$

and whereby Ri are the respective measurement results D1, D2, D3 and S1, S2, S3 and P1, P2, P3. The variation index VI describes the typical deriation of results in the course of the measurement series and is independent on the number of measurements.

For example if it is presumed, that the values of the systolic blood pressure are S1=112 mmHg, S2=124 mmHg and S3=124 mmHg, the mean value is calculated as follows:

$$\text{Mean} = (112+124+124)/3 = 120 \text{ mmHg}$$

In this example the variation index $VI_s$ for the systolic blood pressure consequently is defined as follows:

$$VI_s = 1/n(120-112+124-120+124-20)/120 = 16/120 = 4.4\%.$$

If the variation index is above a variation index limit value, the user/patient is additionally informed by displaying this matter of fact. If the variation index frequently exceeds the predefined limits, the user is advised (operating manual) to undergo further diagnosis.

The variation index limits are typically as follows: 0.10 [%] for the systolic blood pressure, 10 [%].for the diastolic blood pressure and 0.8 [%] for the pulse rate.

Prior to the calculation of averages of the results, it is verified, whether consecutive blood pressure values are sufficiently similar to each other, i.e. it is verified, whether the following condition iii.) is fulfilled:
Condition iii for the Systolic Blood Pressure:

$$S1-18 \text{ mmHg} < S2 < S1+18 \text{ mmHg}$$

$$S2-18 \text{ mmHg} < S3 < S2+18 \text{ mmHg}$$

Condition iii for the Diastolic Blood Pressure:

$$D1-12 \text{ mmHg} < D2 < D1+12 \text{ mmHg}$$

$$D2-12 \text{ mmHg} < D3 < D2+12 \text{ mmHg}$$

If all of the above conditions are fulfilled, it is concluded that the measurement results are correct. Consequently, a normal arithmetic average of the results is calculated as follows:

$$S=(S1+S2+S3)/3$$

$$D=(D1+D2+D3)/3$$

The values S and D are subsequently displayed in the blood pressure measuring device.

The above-mentioned ranges (+/−18 mmHg and +/−12 mmHg are referred to as the similarity limits.

It has been found that similarity limits of +/−18 mmHg for the systolic blood pressure and +/−12 mmHg for the diastolic blood pressure are leading to sufficiently precise results. Other similarity limits could be used as well.

In addition, it is verified, whether or not condition iv.) holds valid. It is checked whether results are highly altered compared to each other. The condition iv.) is defined as follows:
Systolic Blood Pressure:

$$S1+40 \text{ mmHg} < S2 < S1-40 \text{ mmHg}$$

$$S2+40\text{ mmHg} < S3 < S2-40\text{ mmHg}$$

Diastolic Blood Pressure:

$$D1+25\text{ mmHg} < D2 < D1-25\text{ mmHg}$$

$$D2+25\text{ mmHg} < D3 < D2-25\text{ mmHg}$$

If at least one of the above four conditions is fulfilled, it is concluded that at least one of the measurement results is due to an incorrect measurement. The range +−40 mmHg for the systolic blood pressure and +−25 mmHg for the diastolic blood pressure are also referred to as the alteration limits. One can safely assume that values beyond the alteration limits represent artifact. These results are rejected.

If the above condition iv.) is not met, i.e. if all results are not highly altered and if the above condition iii.) is not met, i.e. the results are not sufficiently similar to each other, a weighted average is formed.

It is assumed, that blood pressure results which are neither similar nor highly altered, either represent an artifact or a severe pathologic blood pressure variation. Thus, the influence of these values is reduced by calculating a weighted average as follows:

$$S=2S1+2S2+S3/5, \text{ whereby } S3 \text{ is the non-similar value and}$$

$$D=2D1+2D2+D3/5, \text{ whereby } D3 \text{ is the non-similar value.}$$

In a more general form:

$$S = \frac{A1S1 + A2S2 + A3S3}{A1 + A2 + A3}$$

$$D = \frac{B1D1 + B2D2 + B3D3}{B1 + B2 + B3}$$

whereby $A1>A3$; $A2>A3$ if $S3$ is not similar to $S1$ and $S2$ and $B1>B3$; $B2>B3$ if $D3$ is not similar to $D1$ and $D2$.

The values of A1, A2, A3 and B1, B2, B3, respectively are empirically set to 2 for similar values (e.g. S1 and S2) and to 1 for non similar values. Further findings in research may lead to an amendment of these factors without leaving the scope of the present invention.

In FIG. 3, the most likely causes generating specific blood pressure differences during a series of measurements are graphically shown.

Curve 1 represents the probability of measuring physiologic blood pressure differences. Due to physiologic reasons, small blood pressure differences occur relatively frequently. As long as the differences are within the definitions of similarity, i.e. meet the condition iii.) a normal arithmetic average is made. Generally, in healthy persons physiologic blood pressure changes are small in rest condition.

Relatively large consecutive blood pressure differences which are above the alteration limit, i.e. which meet the condition iv.) are most probably due to artifact. The probability of artifact is shown by curve 3 in FIG. 3. When the results meet condition iv.), by referring to the criteria of high alteration no average is calculated and the values are subsequently rejected.

If none of the conditions iii.) and iv.) are met, i.e. if a result is above the similarity limit but below the alteration limit, the difference may be due to pathologic reasons or to artifact. The probability of blood pressure differences due to pathologic reasons is shown by curve 2 in FIG. 3. In such a case, a weighted average is calculated.

The similarity limits are set to 18 mmHg for the systolic blood pressure and 12 mmHg for the diastolic blood pressure. The alteration limit is set to 40 mmHg for the systolic blood pressure and to 25 mmHg for the diastolic blood pressure.

In case one of the values is rejected, a fourth measurement is initiated. The same analysis, especially verification of the conditions i.), ii.), iii.) and iv.) is applied to the new set of results. If again one value has to be rejected, an error message is displayed and no measurement result is given. If the fourth measurement is not highly altered, i.e. if condition iv.) is not fulfilled, a measurement result is calculated and displayed as described above.

Averages are processed as follows:

After obtaining three blood pressure measurement results, the following cases have to be distinguished.

1) V1(S)V2(S)V3 ⇒ $A_N = \frac{1}{3}(V1+V2+V3)$
2) V1(NS)V2(S)V3 ⇒ $A_W = \frac{1}{5}(V1+2V2+2V3)$
3) V1(HA)V2(S)V3 ⇒ Initiate a fourth measurement and check V2, V3; V4
4) V1(S)V2(NS)V3 ⇒ $A_W = \frac{1}{5}(2V1+2V2+V3)$
5) V1(S)V2(HA)V3 ⇒ Initiate a fourth measurement and check V1, V2, V4
6) V1(NS)V2(NS)V3
   and
   a) V3(S)V1 ⇒ $A_W = \frac{1}{5}(2V1+V2+2V3)$
   and
   b) V3(NS)V1 or
      V3(HA)V1 ⇒ Error display
7) V1(HA)V2(NS)V3
   and
   a) V3(S)V1 ⇒ Initiate a fourth measurement and check V1, V3, V4
   and
   b) V3(NS)V1 or
      V3(HA)V1 ⇒ Error display
8) V1(NS)V2(HA)V3
   and
   a) V3(S)V1 ⇒ Initiate a fourth measurement and check V1, V3, V4
   and
   b) V3(NS)V1 or V3(HA)V1 ⇒ Error display
9) V1(HA)V2(HA)V3
   and
   a) V3(S)V1 ⇒ Initiate a fourth measurement and Check V1, V3, V4
   and
   b) V3(NS)V1 or
      V3(HA)V1 ⇒ Error display whereby V1, V2, V3, V4 designate the values of the systolic or the diastolic blood pressure (S) designates that subsequent values are similar (NS) designates that subsequent values are non-similar (HA) designates that subsequent values are highly altered The method of the present invention is shown in more detail in the flow chart in FIG. 1.

FIG. 1 shows a flow chart of an embodiment of the invention. A blood pressure measuring device may be operated either in a single mode or in an average mode. In the case of single mode operation, the variable meancountend is set to 1. In the case of average mode operation, the variable meancountend is set to the pre-defined number of measurements, e.g. to 3. If the device operates in average mode, measurements are repeated e.g. three times for generating three consecutive results of values for the systolic and for the diastolic blood pressure and pulse frequency. If e.g. three consecutive results of the systolic and the diastolic blood pressure have been obtained, the similarity and the degree of alteration of these values is checked. If similarity of all three values is detected, a conventional average is formed (see left branch of FIG. 1).

If the second result is not similar to both the first and third result, it is checked whether the first and the third results are similar to each other. If the first and the third results are similar, an additional measurment is made. If not, an error is indicated. If an additional measurement is made, a variable, "meanflag" is set to 1. If the variable meanflag has previously been set to 1, an error message is displayed. This means, that in case of non-similar values, only a limited number of, e.g. one repetition may occur.

If the second result is not similar to the first or the third result, it is verified whether the first or the third value is highly altered to the second value. If there is no high alteration, a weighted average is formed. If there is a high alteration, a repetition is initiated in order to acquire an additional measurement result. If an additional measurement is scheduled, the variable meanflag is checked. If the variable meanflag has been previously set to 1, no additional measurement is taken and an error message is displayed.

After calculation of the conventional or of the weighted average and before displaying of the results, the following procedure is performed:

On the basis of the measurement values, it is verified whether the patient is properly settled. If the patient is found to be not properly settled, a no-settling indication is displayed and the patient is asked to properly settle before taking a further measurement.

In addition, the variation index is formed on the basis of the measurement values. If the variation index VI is above the variation index limit $VI_{Limit}$, an error message is displayed.

In other words: after calculation of the average, it is verified whether one the above defined condition i) or condition ii) is fulfilled. If yes an appropriate indication is displayed to the user.

What is claimed is:

1. A method for non-invasively measuring the blood pressure of a patient, comprising the steps of
   a) measuring the diastolic and the systolic blood pressure value and the pulse rate of the patient;
   b) repeating step a) at least once thereby generating a series of consecutive measurement results of the systolic and diastolic blood pressure and of the pulse rate;
   c) automatically analyzing said series of consecutive results for determining the validity of said results by verifying whether a first condition is fulfilled, whereby said first condition is fulfilled if results of the systolic blood pressure are continuously decreasing and if the results of the diastolic blood pressure are continuously decreasing or increasing and if the results of the pulse rate are continuously decreasing.

2. A method according to claim 1, wherein in step c), a variation index of the diastolic blood pressure, the systolic blood pressure and the pulse rate is calculated according to the following formula:

$$VI = \frac{1}{n} \sum_{i=1}^{n} \frac{|R_i - \text{mean}|}{\text{mean}} = \sum_{i=1}^{n} \frac{|R_i - \text{mean}|}{\sum_{i=1}^{n} R_i}$$

$$\text{where mean} = \sum_{i=1}^{n} \frac{R_i}{n}$$

Ri are the respective measurement results and
n is the number of measurements for each series of results of the diastolic blood pressure, the systolic blood pressure and the pulse rate and
whereby it is verified whether a second condition is fulfilled, whereby the second condition is fulfilled if the variation index is above a predetermined variation index limit for at least one of the parameters diastolic blood pressure, systolic blood pressure and pulse rate.

3. A method according to claim 2, comprising the further steps of verifying whether a third condition is fulfilled, whereby the third condition is fulfilled when the differences between subsequent measurement results of the systolic and of the diastolic blood pressure measurement are below a predetermined or predeterminable similarity limit and verifying whether a fourth condition is fulfilled, whereby the fourth condition is fulfilled when the differences between subsequent measurement results of the systolic and the diastolic blood pressure are above a predetermined or predeterminable alteration limit.

4. A method according to claim 1, wherein if the first condition is met,
   a signal is generated advising the user to repeat the measurement or
   an additional measurement is automatically initiated after a predetermined period of time, and/or
   a signal is generated, said signal indicating that the user has not been properly settled to a rest condition in the course of the measurement.

5. A method according to claim 2, wherein if the second condition is met, a message is displayed to the user.

6. A method according to claim 3, wherein if the third condition is met, an arithmetic average of the measurement results of the diastolic blood pressure and of the systolic blood pressure and of the pulse frequency is calculated and displayed and
   wherein if the fourth condition is met, results above the alteration limit are disregarded and a new measurement of the systolic and of the diastolic blood pressure is made and wherein if the third condition is not met, a weighted average of the systolic of the diastolic blood pressure measurement results and the pulse frequency result is calculated.

7. A method according to claim 1, wherein in step a), the diastolic and the systolic pressure value and the pulse rate are measured by an oscillometric method.

8. A device for non-invasively measuring the blood pressure of a patient, the device comprising
   means for non-invasively measuring the systolic and the diastolic blood pressure and pulse rate of a patient;
   means for storing a series of consecutive measurement results of the systolic blood pressure, the diastolic blood pressure and the heart rate;
   means for analyzing the series of measurement results of the diastolic, the systolic blood pressure and the pulse rate,
wherein the means for analyzing are adapted to determine whether the results of the systolic blood pressure are continuously decreasing and the results of the diastolic blood pressure are continuously increasing or decreasing and the results of the pulse rate are continuously decreasing.

9. A device according to claim 8, wherein the means for analyzing are adapted to calculate a variation index for each of the systolic blood pressure, the diastolic blood pressure and the pulse rate according the following formula:

$$VI = \frac{1}{n} = \sum_{i=1}^{n} \frac{|R_i - \text{mean}|}{\text{mean}}, \text{ where mean} = \frac{1}{n}\sum_{i=1}^{n} Ri$$

wherein the means for analyzing are further adapted to verify whether the variation index is above a predetermined or predeterminable variation index limit.

10. A device according to claim 8, wherein the means for analyzing are further adapted to verify whether the differences between consecutive results of the systolic blood pressure and of the diastolic blood pressure are above a predetermined or predeterminable alteration limit or below a predetermined or predeterminable similarity limit.

11. A device according to claim 8, wherein the device further comprises means for forming an average of measurement results of the systolic blood pressure and the diastolic blood pressure and means for forming a weighted average of the measurement results of the systolic blood pressure and of the diastolic blood pressure.

* * * * *